United States Patent [19]
Elstrom, deceased et al.

[11] 4,204,053

[45] May 20, 1980

[54] METHOD FOR THE PRODUCTION OF UREA OF HIGH MECHANICAL STRENGTH

[75] Inventors: Tore Elstrøm, deceased, late of Porsgrunn, Norway, by Britt Elstrøm, administrator; Per F. Gustavsen, Skien; Olav Kjøhl, Porsgrunn, both of Norway

[73] Assignee: Norsk Hydro a.s., Oslo, Norway

[21] Appl. No.: 942,498

[22] Filed: Sep. 13, 1978

[30] Foreign Application Priority Data

Sep. 19, 1977 [NO] Norway ................................ 773201

[51] Int. Cl.$^2$ ............................................. C08G 12/12
[52] U.S. Cl. ................................................... 528/259
[58] Field of Search ............................ 528/230, 259

[56] References Cited

FOREIGN PATENT DOCUMENTS

1296937 11/1972 United Kingdom ..................... 528/230

OTHER PUBLICATIONS

Walker, J. Frederic, Formaldehyde (3rd Ed), American Chemical Society Monograph Series, No. 159, Reinhold Co., N.Y., 1964, p. 142, table 59.

*Primary Examiner*—Lucille M. Phynes

[57] ABSTRACT

A method for the production of urea of high mechanical strength by the crystallizing process or the evaporation process, including a prilling or granulating step, utilizing 0.01-1% by weight of formaldehyde in the form of a formaldehyde polymer, which comprises, before prilling or granulating, incorporating in the urea, a formaldehyde polymer with a formaldehyde content of 82-97% and with a melting point of about 90°-160° C.

5 Claims, No Drawings

METHOD FOR THE PRODUCTION OF UREA OF HIGH MECHANICAL STRENGTH

The present invention concerns a method for the production of urea of high mechanical strength. The method comprises the use of 0.01–1% by weight of formaldehyde in the form of a formaldehyde polymer.

Today there are increasing demands concerning the mechanical strength of urea. The reasons for this are several; firstly urea is exposed to great mechanical strains due to the methods of handling and transporting used today, and this may lead to crushing of the urea granules and thus a greater possibility for dust formation. Secondly the requirements for a non-dusting product during handling have become increasingly severe.

It has for a long time been customary to add formalin corresponding to ca. 0.5% formaldehyde to the urea raw liquor to improve the mechanical strength of the urea granules. This method is essentially covered by what is known from Swiss Pat. No. 363.974. From this patent it is known to add formaldehyde in the form of a 37% formalin solution to the urea raw liquor before evaporation and prilling. It is preferably added 0.5–5% by weight of formaldehyde based on the weight of urea. The finished urea product is reported to have a compressive strength of 700–750 g when 3% formaldehyde is utilized. The addition of formaldehyde is primarily used to improve the storing properties of the product.

From British Pat. No. 875.730 it is known a method for preventing baking of urea where formaldehyde in the form of formalin, gaseous formaldehyde, paraformaldehyde or a paraformaldehyde solution is evenly distributed in the mass of urea. The amount of formaldehyde used is 1 mol formaldehyde per 50–100,000 moles of urea.

The examples given in the patent only describe formalin addition to dry urea or to aqueous urea slurry, for example in a crystallizing vessel. Nothing is mentioned in the patent regarding the mechanical strength of the product, but the tendency of the urea to cake is said to be substantially eliminated utilizing the described method.

To prevent baking of urea it is further known from British Pat. No. 1.296.937 to add 0.01–0.4% by weight of dry, granular paraformaldehyde to dry, granular urea to form a layer on the outer surface of the urea particles.

The method according to the mentioned Swiss Patent is in connection with the evaporation process giving a satisfactory product which may be handled in bulk form without too much dust formation.

A substantial amount of the urea is produced by the socalled crystallizing process, among others to obtain a product with low content of biuret. If in a such process, there is incorporated ca. 0.5% formaldehyde in the form of formalin in the melt or in the crystals, the water content of the end product will increase by 0.8%. 0.5% formalin addition will give the end product a water content of at least 1%. This increase in water content is undesirable because a major requirement for satisfactory storing conditions for urea is that the product should not contain more than 0.2–0.3% water. Even then, an anticaking agent should usually be utilized to obtain a satisfactory result. It was therefore soon evident that the use of formalin in a crystallizing process would require an extra drying step before the product was sent for storage.

The main purpose of the invention was therefore to provide a method for the production of urea with high mechanical strength and at the same time with a low tendency for caking.

An additional object of the invention was to provide a method suitable for the crystallizing process as well as for the evaporation process for production of urea.

Due to the positive results from the experiences with the formalin addition in the evaporation process, tests were conducted to see if formaldehyde could be added to urea in other forms and at different stages in the urea production process. Incorporation of gaseous formaldehyde soon gave such severe practical and environmental problems, that such tests were not carried out further.

The addition of paraformaldehyde to solid urea such as described in the British Pat. No. 1.296.937 does not solve the problems concerning the required mechanical strength. Even if the surface of the urea granules is covered with a layer, the particle strength will be too weak to withstand crushing and resultant dusting during modern bulk handling.

The British Pat. No. 875.730, which also relates to a method to prevent caking of urea, mentions paraformaldehyde as a type of formaldehyde which may be used. The patent gives, however, no indications of how the mechanical strength of the urea particles may be improved. In spite of this the inventors still investigated whether a formaldehyde polymer, for example paraformaldehyde, advantageously could be used to improve the mechanical strength of the urea particles. These tests showed among other facts, that one can not substitute formalin with any type of formaldehyde polymer. Neither is any type of paraformaldehyde, which is a formaldehyde polymer with the degree of polymerization of 8–100, suitable. To obtain the lowest possible water content in the product, apparently one should use a formaldehyde polymer with the highest possible content of $CH_2O$. We have, however, found that a formaldehyde polymer with a very high content of $CH_2O$ is not suitable. The melting point of the formaldehyde-polymer used is also important, it should not be too high. Further it has been found that it is not insignificant at which step in the process the formaldehyde is incorporated. It seems that the content of free ammonia and ammonium cyanate will not be the same in for example a urea raw liquor, a urea melt and the crystal solution which is conveyed to the melting stage.

An explanation of what is here experienced, may be that highly concentrated formaldehyde polymer will not dissolve or depolymerize rapidly enough under the conditions one usually experiences in a process for the production of urea prills. If one assumes that the rate of solution of formaldehyde polymer is a function of the degree of polymerization, the lower limit for a utilizable formaldehyde polymer will be determined by weighing its rate of solution and its water content. Using the test results and the above hypothesis it is found that formaldehyde polymer with a $CH_2O$-content of 82–97% and with a melting point in the area of 90°–160° C. is suitable to increase the mechanical strength of the urea particles.

It has further been found that formaldehyde polymer with too low a melting point will give too much water and gas formation, while with a too high melting point the time needed for going into solution will be too long. Using a formaldehyde polymer with 97% $CH_2O$ one must accordingly use one with relatively low melting point, for example 145° C. The degree of polymerization should be below 40 and preferably between 15 and 25.

Using a formaldehyde polymer according to the invention in place of formalin one obtains urea with at least as high mechanical strength, the same amounts added calculated on a pure $CH_2O$ basis. In addition the use of formaldehyde polymer gives urea with better storage properties than what is obtained with formalin.

The particle strength of urea prills may be denoted as % of crushed material formed with a special "gun test". This "gun test" briefly consists in that the particles from a choosen sieve fraction by the help of a venturi tube is fed into a stream of air with a fixed velocity. The stream of air will cause the particles to collide with a smooth metal plate surrounded by a 0.5 mm sieve. Crushing and dust formation is determined in a subsequent sieve analysis. This method has shown to give a good degree of reproducibility and a representative expression of the particles' brittleness.

Utilizing the above mentioned test it has been found that urea produced utilizing 0.2% $CH_2O$ as formaldehyde polymer gives 50% crushed product, while in urea produced utilizing formalin one has to use up to 0.5% $CH_2O$ to obtain prills with similar strength. The explanation why addition of formaldehyde polymer seems to give urea prills of higher mechanical strength than prills produced with the addition of formalin, may be that $CH_2O$-addition takes place during different steps in the process and that the ammonia and ammonium cyanate content during these steps are different.

Theoretically $CH_2O$ may react with the reactants present, as ammonia and urea, according to different equations. From the measurements of, among others, the water content in the urea products, it seems probable that the component which is responsible for the improvement of particle strength will not be the same utilizing formalin and formaldehyde polymer as $CH_2O$-source the evaporation process and in the crystallizing process respectively. The inventors do not want to limit the concept by an special explanation of what the results recorded, still it seems correct to assume that the significant particle strength improving component is obtained by condensation during the reaction between methylol urea formed the reaction between $CH_2O$ and urea when formaldehyde polymer is used according to the examples. When formalin is added to the urea raw liquor, however, the particle strength improving component seems to be hexamethylentetramine.

The method according to the invention is as defined in the accompanying patent claims. Otherwise the method is described in detail in the examples below.

EXAMPLE 1

During production of prilled urea from evaporated urea melt, a 0.05 to 0.6% formaldehyde polymer was added immediately before prilling, the formaldehydepolymer having a formaldehyde polymer content of 92%. Immediately after, prilling tests of the products were made. Test products were cooled and a particle fraction between 1.4 and 2 mm was isolated by sieving. The brittleness of the urea particles was determined by help of the "gun test" described above.

The fraction crushed to smaller particles than 1.4 mm was determined. Likewise the formation of dust particles with the diameter less than 0.5 mm was determined. The results are given in Table 1.

EXAMPLE 2

In completely dried urea crystals with the temperature of 70°–80° C., there was incorporated from 0.05 to 0.30% formaldehyde polymer with the formaldehyde content of 92%. The resulting mixtures were melted and thereafter prilled. After prilling tests were taken from the finished product. The further treatment was as described in Example 1.

The results of the "gun test" is given in Table 1.

EXAMPLE 3

To study the effect of the formaldehyde the strength of prills with the low content of free ammonia and ammonium cyanate, the crystallizing apparatus were fed with the urea solution with lower content of these two components than what is considered as normal for this type of process.

In the completely dried urea crystals were incorporated from approx. 0.2 to approx. 0.4% formaldehyde polymer as in the examples above. After melting and prilling of these mixtures the particle strength was determined as described above.

The results are given in Table 1. From this Table we can see that the improvement in particle size is significantly higher when the content of free ammonia and ammonium cyanate is low.

Table 1

| | The improvements obtained by addition of formaldehyde polymer in the production of urea prills | | | |
|---|---|---|---|---|
| Process | % Content of $CH_2O$ | A<br>% Reduction in crushed material | B<br>% Reduction of dust | C<br>Single particle strength kg |
| Evaporation Example 1 | 0.00 | 0 | 0 | 0.4 |
| | 0.11 | 25 | 20 | |
| | 0.30 | 53 | 50 | 0.6 |
| | 0.39 | 70 | 60 | |
| | 0.50 | 92 | 70 | 0.8 |
| Crystal Example 2 | 0.00 | 0 | 0 | 0.4 |
| | 0.16 | 36 | 30 | |
| | 0.24 | 50 | 40 | 0.7 |
| | 0.31 | 60 | 55 | |
| | 0.37 | 77 | 60 | 0.9 |
| Crystal Example 3 | 0.00 | 0 | 0 | 0.4 |
| | 0.23 | 62 | 53 | 0.8 |
| | 0.31 | 80 | 70 | 0.8 |
| | 0.39 | | | 0.9 |

A = % Reduction ($R_1$) in crushed material and is calculated as follows:
% $R_1$ = (% $N_{UF}$ − % $N_F$) · $K_1$
% $N_{UF}$ = % crushed in test without $CH_2O$
% $N_F$ = % crushed in test with $CH_2O$
$K_1$ = Constant dependant of air velocity used in "gun test"
B = % Reduction ($R_2$) in amount of dust, calculated from formulae
% $R_2$ = (% $S_{UF}$ − % $S_F$) · $K_2$
% $S_{UF}$ = % dust in test without $CH_2O$
% $S_F$ = % dust in test with $CH_2O$
$K_2$ = Constant dependant of air velocity used in "gun test"
C = Strength of single particles denoted by the force in kg required to crush particle sizes of ca. 1.6 mm. This method of measurement is described of J. O. Hardesty and W. H. Ross in Ind. Eng. Chem.- vol. 30, s. 668–72 (1938).

As it is shown in the Table one obtains a significant reduction in crushed amount and in amount of dust by the addition of formaldehyde polymer. The strength of the urea prills is thus so much improved by the utilization of formaldehyde polymer that such prills may be exposed for modern transport and handling methods without inconvenient dust formation and reduction in particle size. By experience a value of C of 0.4 kg will give excessive dust and such product will not be suitable for bulk handling.

The Table further denotes that by the evaporation process it has to be utilized some more formaldehyde polymer than with the crystallizing process to obtain equal beneficial results. The values for the evaporation process are still fully comparable with the values one obtains using formalin according to the Swiss Pat. No. 363,974. The use of formalin is furthermore less adventageous in many other ways.

We claim:

1. A method for the production of urea of high mechanical strength by the crystallizing process or the evaporation process, including a prilling or granulating step, utilizing 0.01–1% by weight of formaldehyde in the form of a formaldehyde polymer, which comprises, before prilling or granulating, incorporating in the urea a formaldehyde polymer with a formaldehyde content of 82–97% and with a melting point of about 90°–160° C.

2. A method according to claim 1, wherein a formaldehyde polymer with a formaldehyde content of 90–96% and with a melting point of 120°–150° C. is used.

3. A method according to claim 1, wherein a formaldehyde polymer with a formaldehyde content of 90–92% and with the melting point of 120°–140° C. is used.

4. A method according to claims 1 or 3, wherein the formaldehyde polymer is added to the urea melt.

5. A method according to claims 1 or 3, wherein urea is produced by the crystallizing process and the formaldehyde polymer is added to the crystals before melting.

* * * * *